US008359170B2

(12) United States Patent
Gunasekaran et al.

(10) Patent No.: US 8,359,170 B2
(45) Date of Patent: Jan. 22, 2013

(54) LASER-BASED ULTRASONIC MEASUREMENTS OF CELLULAR CERAMIC BODIES DURING THERMAL PROCESSING

(75) Inventors: Natarajan Gunasekaran, Painted Post, NY (US); Zhiqiang Shi, Painted Post, NY (US); James Arthur Smith, Idaho Falls, ID (US)

(73) Assignee: Corning Incorporated, Corning, NY (US)

( * ) Notice: Subject to any disclaimer, the term of this patent is extended or adjusted under 35 U.S.C. 154(b) by 281 days.

(21) Appl. No.: 12/787,517

(22) Filed: May 26, 2010

(65) Prior Publication Data

US 2010/0305877 A1 Dec. 2, 2010

Related U.S. Application Data

(60) Provisional application No. 61/182,428, filed on May 29, 2009.

(51) Int. Cl.
 *G06F 19/00* (2011.01)
(52) U.S. Cl. .......................................... 702/39
(58) Field of Classification Search ............ 702/39
 See application file for complete search history.

(56) References Cited

U.S. PATENT DOCUMENTS

2007/0114700 A1 5/2007 Andrewlavage, Jr. et al.
2007/0266547 A1 11/2007 Shi

OTHER PUBLICATIONS

David W. Blodgett and Kevin C. Baldwin, Laser-Based Ultrasonics: Applications at APL, Johns Hopkins APL Technical Digest, vol. 26, No. 1 (2005), p. 36-45.*
Lasson Technologies: www.lasson.com.
C.B. Scruby and L.E. Drain, Laser-Ultrasonics: Techniques and Applications, Adam Hilger, 1990—Book.

* cited by examiner

*Primary Examiner* — Tung S Lau
(74) *Attorney, Agent, or Firm* — Timothy M. Schaeberle

(57) ABSTRACT

Laser-based ultrasonic (LBU) systems and methods for measuring at least one material property of a ceramic cellular ceramic body during thermal processing are disclosed. The method includes subjecting the ceramic cellular ceramic body to a temperature cycle within an interior of an oven. For a plurality of temperatures within the temperature cycle, the cellular ceramic body is irradiated with a modulated laser beam to generate acoustic waves in the cellular ceramic body over a plurality of acoustic paths. The method also includes sequentially irradiating the cellular ceramic body using a detection laser beam so that the acoustic waves are detected. The method also includes calculating from the detected acoustic waves at least one material property of the ceramic cellular body as a function of temperature.

20 Claims, 18 Drawing Sheets

LASER-BASED ULTRASONIC MEASUREMENTS OF CELLULAR CERAMIC BODIES DURING THERMAL PROCESSING

CROSS-REFERENCE TO RELATED APPLICATIONS

This application claims the benefit of priority under 35 U.S.C. §119(e) of U.S. Provisional Application Ser. No. 61/182,428 filed on May 29, 2009, which application is incorporated by reference herein.

FIELD

The present disclosure relates to measuring properties of cellular ceramic bodies such as used to form particulate filters, and in particular relates to measuring cellular ceramic bodies during thermal processing.

BACKGROUND

Ceramic bodies having cellular (e.g., honeycomb) structures are used to form particulate filters for a variety of filter-based applications, such as vehicular exhaust systems, to reduce pollutants. Such structures generally comprise a network of interconnected web walls that form a matrix of elongated, gas-conducting cells that may have, for example, a square, octagonal or hexagonal cross-sectional shape. A cylindrical outer skin that is integrally connected to the outer edges of the web walls surrounds the network of web walls such that a round-shaped or an oval-shaped cross-sectional structure is formed having opposing inlet and outlet ends for receiving and expelling exhaust gases through the matrix of cells.

It is useful to be able to measure and characterize various properties of ceramic bodies without damaging or destroying the cellular ceramic body. Such measurement and characterization assist in determining whether there are faults (e.g., cracks or fractures, deformities, density variations, etc.) and whether the product conforms to the design specifications. Generally, such measurements provide insight into the manufacturing process and can be used to improve the process. It would be particularly useful to measure and characterize various properties of the ceramic bodies during thermal processing, such as scintering or thermal shock testing, where the ceramic body is not readily accessible to measurement.

One particularly useful property of a ceramic body is its "specific modulus," which is a measure of an object's ability to be non-permanently deformed and can be considered an indicator of the object's resistance to breakage. The specific modulus of a material is essentially the elastic (Young's) modulus divided by the material's density. This parameter is useful in comparing different materials in designing the ceramic body. The specific modulus of an object can be determined by measuring the strain placed on the object in response to an applied stress, normalized by the object's density. The specific modulus of a ceramic body yields information about its composition, its brittleness, etc. The measured specific modulus can also be compared to a specified value to assess whether a particular ceramic body, such as a diesel particulate filter (DPF) meets production specifications.

SUMMARY

One aspect of the disclosure relates to A method of measuring at least one material property of a ceramic cellular ceramic body during thermal processing. The method specifically comprises the following steps: a) subjecting the ceramic cellular ceramic body to a temperature cycle within an interior of an oven having first and second windows; b) sequentially irradiating with a first laser beam the cellular ceramic body through the first window at one or more first locations to generate acoustic waves in the cellular ceramic body; c) sequentially irradiating with a second laser beam the cellular ceramic body through the second window at one or more second locations that correspond to the one or more first locations to detect the acoustic waves in the cellular ceramic body; and, d) calculating from the one or detected acoustic waves the at least one material property.

Another aspect of the disclosure relates to a laser-based ultrasonic system for measuring at least one material property of a ceramic cellular ceramic body during thermal processing. The system includes the following components: a) an oven having first and second windows and an interior, and containing in the interior the ceramic cellular ceramic body, the oven being configured to subject the ceramic cellular ceramic body to a temperature cycle; b) a laser generator system configured to generate and sequentially direct a first modulated laser beam through the first window and onto the cellular ceramic body at a plurality of first locations so as to generate acoustic waves over a plurality of acoustic paths within the cellular ceramic body; c) a laser detector system configured to generate and sequentially direct a second laser beam through the second window and onto the cellular ceramic body at a plurality of second locations that correspond to the plurality of first locations so as to detect the acoustic waves and form therefrom a corresponding plurality electrical detector signal representative of the detected acoustic waves; and, d) a processor configured to receive and process the electrical detector signals and calculate the at least one material property.

These and other advantages of the disclosure will be further understood and appreciated by those skilled in the art by reference to the following written specification, claims and appended drawings.

DETAILED DESCRIPTION

Reference is now made in detail to example embodiments of the disclosure, examples of which are illustrated in the accompanying drawings. Whenever possible, the same or like reference numbers and symbols are used throughout the drawings to refer to the same or like elements or components. Cartesian coordinates are provided in some Figures for the sake of reference.

Figure 1:
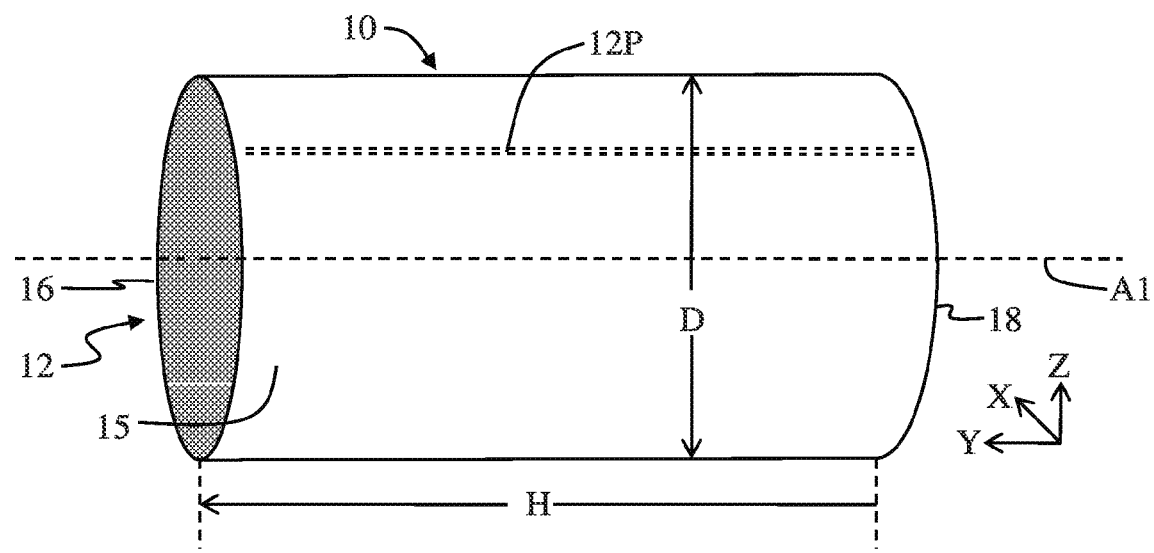
FIG. 1 is a perspective view of an example embodiment of an ultrasonic measurement system used to perform the methods of the present disclosure, shown with a cellular ceramic body operably arranged therein.
Figure 2:
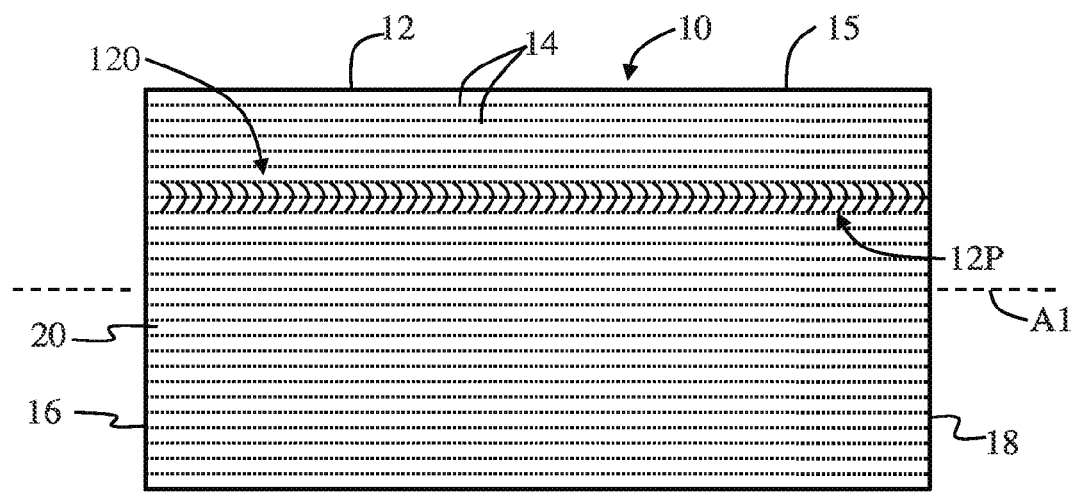
FIG. 2 is a side view of the ultrasonic measurement system and the cellular ceramic body of FIG. 1, showing ultrasonic waves passing through a longitudinal portion of the cellular ceramic body.

FIG. 1 is a perspective view and FIG. 2 is a cross-sectional view (taken in the Y-Z plane) of an example embodiment of a ceramic article 10. Ceramic article 10 comprises a cellular ceramic body 12 having an axial height H and a central axis A1 that defines an axial (longitudinal) direction. Cellular ceramic body 12 is formed by a matrix of intersecting, thin, porous walls 14 surrounded by an outer wall 15. Walls 14 extend across and between opposing ends 16 and 18, and form a large number of adjoining hollow passages or "cells" 20 that also extend between, and are open at, end faces 16 and 18.

Figure 3:
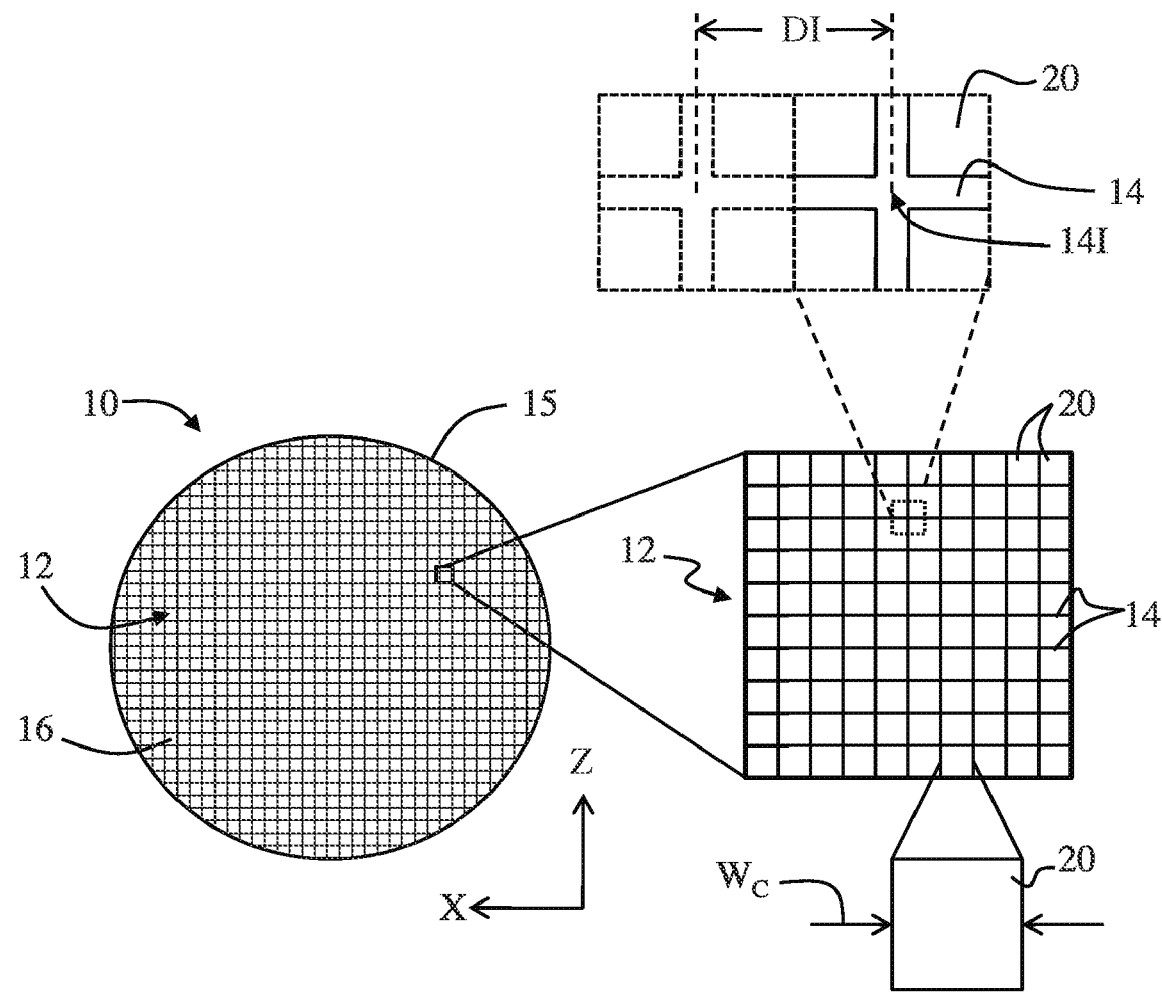
FIG. 3 is a close-up view of an input end of the cellular ceramic body and includes close-up insets that show an example single cell and wall intersections.

FIG. 3 is a close-up view of an input end of cellular ceramic body 12 with insets showing details of walls 14 and cells 20. Intersecting walls 14 form corresponding wall intersections 14I separated by substantially uniform distances DI. In an example embodiment, ceramic article 10 is used to form a flow-through catalyst filter and has, for example, between 100 to 900 cells per square inch, which translates into a cell width $W_C$ that can range from between about 2.5 mm to about 0.85 mm. Walls 14 of such a ceramic article 10 are typically rendered quite thin, e.g., on the order of 2-10 mils thick, or even 2-6 mils thick. Other filter types (e.g., smoke-stack filters) utilize ceramic bodies 10 having on the order of 50 cells per square inch, which translates into a cell width of about 3.6 mm.

An example ceramic article 10 used to form a diesel particulate filter has between about 100 and 400 cells per square inch and walls 14 that are generally thicker, e.g., on the order of 10-25 mils thick, or even 12-16 mils thick. The corresponding cell widths $W_C$ are in the range from about 8 mm to about 1.25 mm.

Ceramic article 10 is manufactured, for example, by extruding a plasticized ceramic-forming precursor of cordierite, mullite, silicon carbide, or aluminum titanate through an extrusion die. The extruded "green body" is then cut and dried. Such green bodies are quite fragile and must be transported to an oven (e.g., a kiln) for thermal processing, wherein the heat transforms the relatively soft and fragile green body into hardened, fired ware with rigid cellular ceramic body 12. Other thermal processing includes, for example, thermal testing of a part. This may include, for example, subjecting the part to thermal shock either by rapid heating, by rapid cooling, or by both rapid heating and cooling.

During the manufacturing process, inhomogeneities can and do occur in cellular ceramic body 12. Such inhomogeneities include, for example, wall thickness variations within the interior of the structure, wall orientation and/or waviness and geometrical deformities. The inhomogeneities also include microstructural variations such as density differences, variations in porosity, microcracks, variations in amounts of microcracks, as well as macroscopic cracks in both the radial and axial directions. These inhomogeneities and variations impact the structural integrity of cellular ceramic body 12 and influence the value of the elastic (and specific) modulus of the cellular ceramic body. Some of these inhomogeneities arise and change during the thermal processing of cellular ceramic body 12, so that it is desirable to measure such properties during thermal processing.

Figure 4:
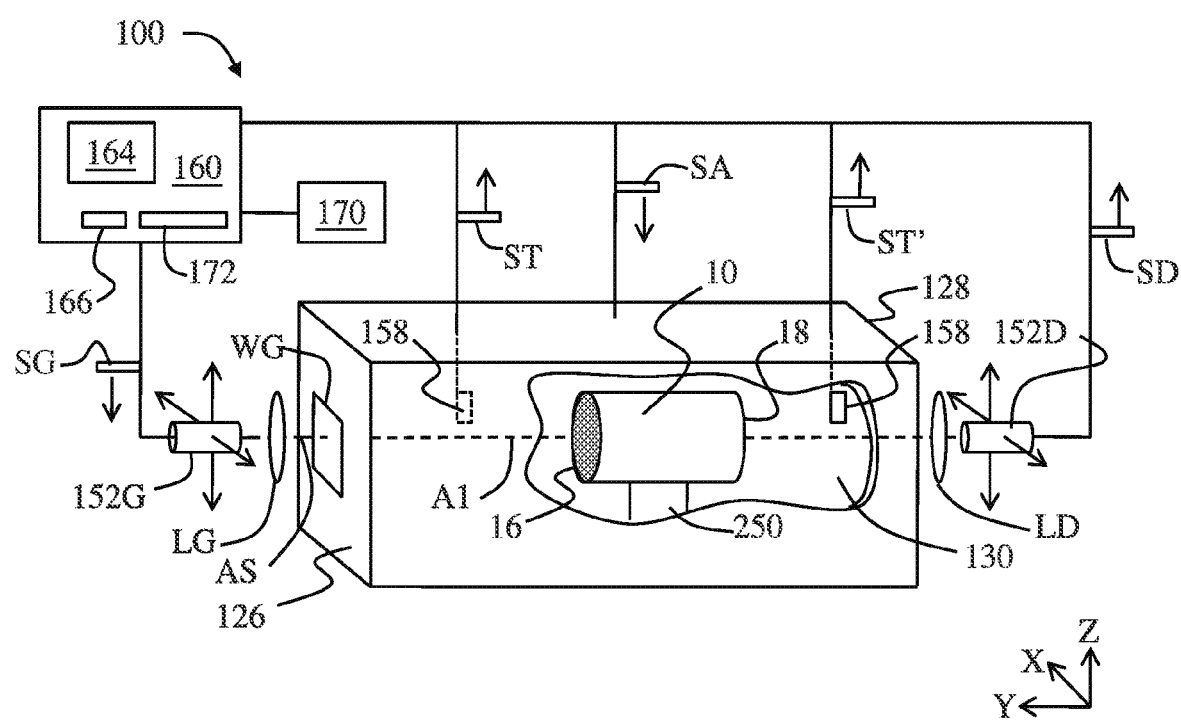
FIG. 4 is a schematic diagram of an example laser-based ultrasonic (LBU) measurement system 100 according to the present disclosure.

FIG. 4 is a schematic diagram of an example laser-based ultrasonic (LBU) measurement system ("LBU system") 100 according to the present disclosure. LBU system 100 includes an oven 120 with respective ends 126 and 128, a length LO, and an interior 130 configured to support a cellular ceramic body 12 to be thermally processed. In an example embodiment, oven 120 comprises a kiln and can support interior temperatures in excess of 1,000° C. Oven 120 is configured to have an adjustable temperature and provide one or more select temperature cycles T(t).

Oven 120 includes windows WG and WR at respective ends 126 and 128 that allow for optical communication with oven interior 130 and in particular with cellular ceramic body 12 therein. In an example embodiment, windows WG and WR comprise fused silica glass that transmits light at 1064 nm and 1550 nm wavelengths, which are common laser wavelengths used in LBU. Fused silica windows can also withstand the relatively high temperatures associated with high-temperature thermal processing such as scintering, and also contribute to maintaining thermal uniformity within oven interior 130, i.e., they are reasonably good thermal insulators and do not contribute significantly to heat loss. In addition, such windows tend to maintain their clarity even when subjected to high temperatures such as temperatures of 1,000° C. and greater.

LBU system 100 also includes a laser generator system ("generator") 152G that generates acoustic waves in cellular ceramic body 12, and a laser detector system ("detector") 152D that detects the acoustic waves, as described below. Generator 152G and detector 152D are respectively arranged at oven ends 126 and 128 adjacent respective windows WG and WD.

In an example embodiment, generator 152G and detector 152D are generally aligned along a system axis AS that is generally aligned in the direction of a cellular ceramic body central axis A1, and are preferably precisely aligned relative thereto. A focusing optical system LG having a focal length FG is arranged between generator 152G and window WG, while another focusing optical system LD having a focal length FD is arranged between detector 152D and window WD.

System 100 preferably includes at least one temperature sensor 158, such as a K-type thermal couple, to measure the oven interior temperature. In an example embodiment, at least one additional temperature sensor 158 is arranged in proximity of, in contact with or internal to cellular ceramic body 12 in order to measure its temperature.

With continuing reference to FIG. 4, in an example embodiment, generator 152G and detector 152D are configured to be moved (e.g., stepped) in corresponding X-Z planes by increments of Δ (e.g., ΔX and ΔZ in the X and Z directions, respectively), wherein in one example Δ=DI. In an example embodiment, generator 152G and detector 152D are configured to be moved in a single direction, such as the X-direction or the Y-direction, and windows WT and WL are elongate in the single direction, i.e., in the X-direction or the Y-direction.

Generator 152G and detector 152D are each electrically connected to a controller 160 that includes a digital processor unit ("processor") 164 configured to receive and process electrical detector signals SD produced by detector 152D, temperature signals ST and ST' produced by temperature sensors 158, as discussed below. Processor 164 is configured to process detector signals SD and calculate at least one material parameter of cellular ceramic body 12, as discussed in detail below. Processor 164 is further configured to use oven temperature information from at least one of signals ST and ST' to correlate the at least one material parameter with a given temperature in temporal temperature cycle T(t).

Oven 120 is also connected to controller 160 and is activated thereby via an oven activation signal SA, which initiates and controls the oven's temperature cycle T(t).

In an example embodiment, controller 160 includes a memory unit 166 electrically connected to processor 164 and configured as a computer-readable medium for storing data and other information (e.g., processed data, computer-readable instructions, software, raw data from electrical signals SD, ST, etc.). In an example embodiment, system 100 includes a display 170 operably connected to controller 160 and configured to display visual and/or graphical representations of information (data) obtained by the ultrasonic measurements of one or more cellular ceramic bodies 12. In an example embodiment, controller 160 is or includes a programmable computer having digital processing capability (e.g., via processor 164) such as a desktop computer, laptop computer, or a work station. In an example embodiment, processor 164 is configured to run image-processing software stored in memory unit 166, such as WiT, available from Dalsa Corporation of Ontario, Canada, and signal analysis software, such as Matlab, C++, such as available from The Mathworks Inc., Natick, Mass.

Figure 5:
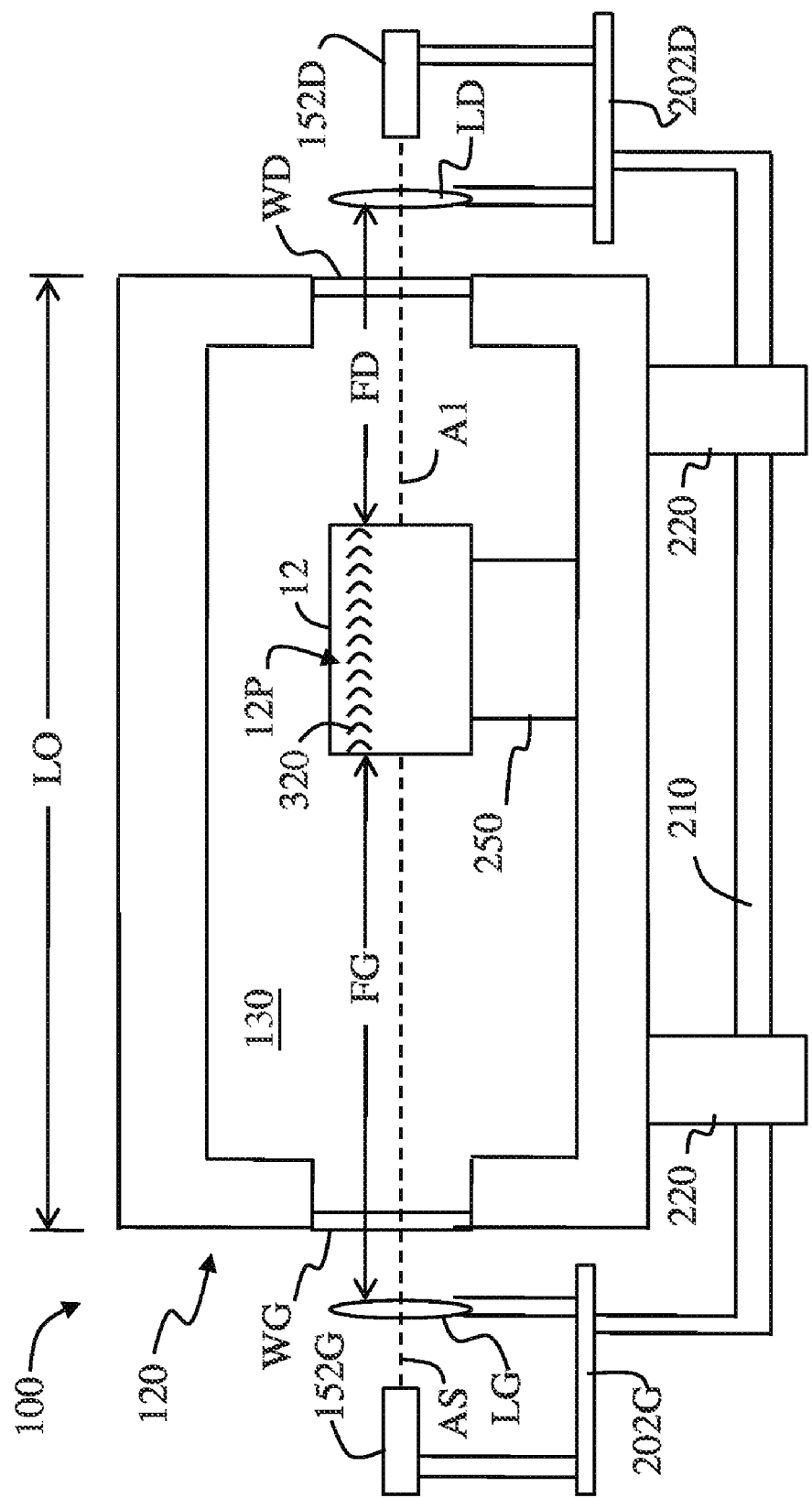
FIG. 5 is a more detailed schematic view of the LBU measurement system of FIG. 4.

FIG. 5 is a more detailed schematic view of system 100 that includes a cross-sectional view of oven 120 as taken in the Y-Z plane. A first translation stage 202G supports generator 152G and focusing optical system LG, while a second translation stage 202D supports detector 152D and focusing optical system LD. In an example embodiment, translation stages 202G and 202D are operably (e.g., mechanically) connected, e.g., via a connection member 210 that runs beneath oven 120, which in an example embodiment is supported above the floor by support members 220.

Cellular ceramic body 12 is supported within oven interior 130 by a support fixture 250. In one example, support fixture 250 supports cellular ceramic body 12 as shown in FIG. 5, with central axis A1 arranged along the Y-direction, i.e., parallel to (or coaxial with) system axis AS. In another example, support fixture 250 supports cellular ceramic body 12 with central axis A1 running along the Z-direction, i.e., perpendicular to system axis AS.

Figure 6:
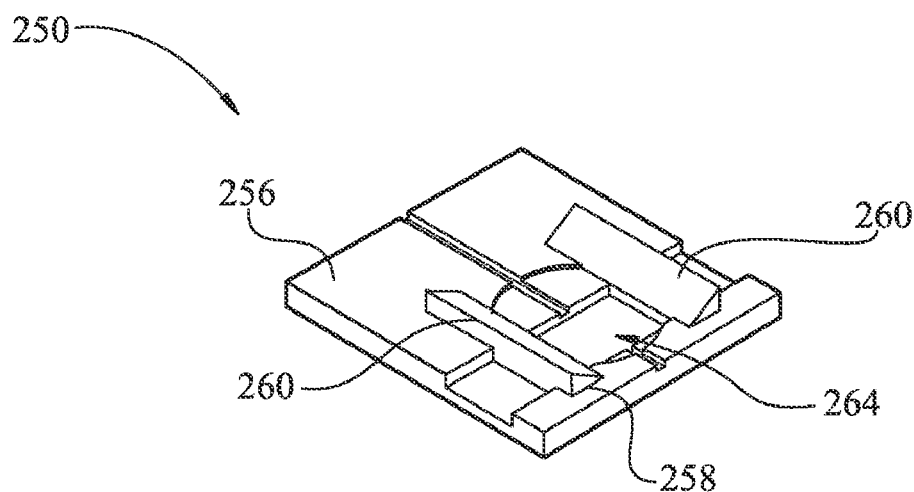
FIG. 6 through FIG. 8 are perspective views of example support fixtures for supporting the cellular ceramic body within the oven interior of the LBU measurement system.

FIG. 6 is a perspective view of an example support fixture 250 that includes base plate 256 with grooves 258 formed therein sized to accommodate respective bottom portions of wedge-shaped support members 260. Support members 260 are spaced apart in opposition to form a valley 264 that accommodates a portion of cellular ceramic body 12. In an example embodiment, base plate 256 and support members 260 are machined from a refractory material such as alumina, which can withstand high oven temperatures (e.g., in excess of 1,500° C.). Support fixture 250 of FIG. 6 is contemplated for use for larger-diameter cellular ceramic bodies, e.g., 7" in diameter.

Figure 7:
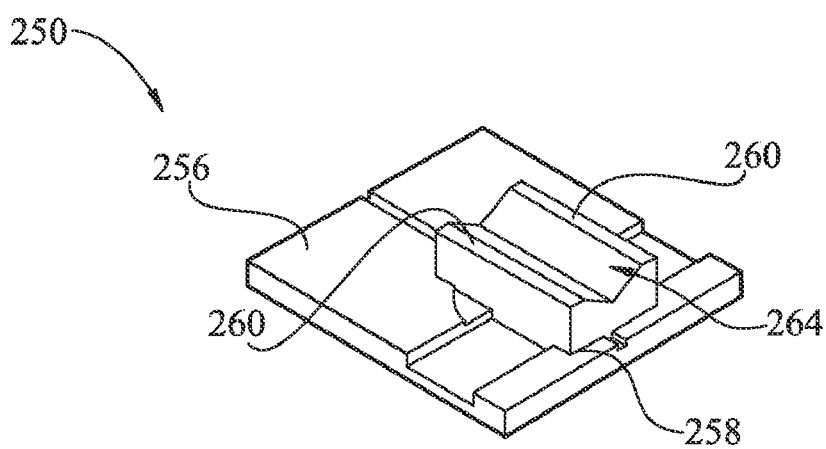

FIG. 7 is a perspective view of an example support fixture 250 similar to that of FIG. 6, but wherein there is only one support member 160 formed to have a V-shaped valley 264 that accommodates a smaller cellular ceramic body than the support fixture of FIG. 6, such as those cellular ceramic bodies having diameters of 3.5" or so.

Figure 8:
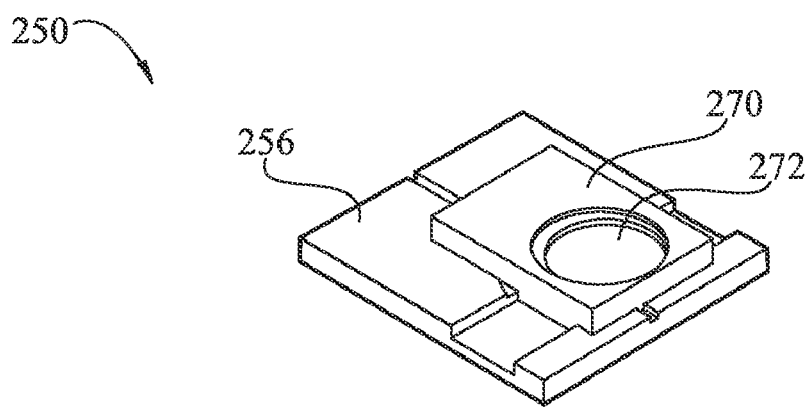

The support structures 250 of FIG. 6 and FIG. 7 are configured to horizontally support a cellular ceramic body 12, i.e., with its central axis A1 in the Y-direction. FIG. 8 is a perspective view of another example support fixture 250 used to support cellular ceramic body 12 in the vertical direction, i.e., with its central axis A1 in the Z-direction. Support fixture 250 of FIG. 8 includes a second plate 270 secured to the base plate and that includes an indentation sized to accommodate an end 16 or 18 of cellular ceramic body 12 and keep the cellular ceramic body standing vertically without the need for additional support.

LBU Measurement Methods

With reference again to FIG. 4 and FIG. 5, cellular ceramic body 12 is placed in oven interior 130 in a select orientation (e.g., horizontal or vertical) using the appropriate support structure 250 (see FIGS. 6 through 8). Cellular ceramic body 12 is then aligned with generator 152G and detector 152D, e.g., by adjusting support fixture 250 and/or by adjusting translation stages 202T and 202R. Oven 120 is then closed and controller 160 activates oven 120 via oven activation signal SA, which causes the oven to initiate a temperature cycle T(t) for thermal processing of cellular ceramic body 12. LBU acoustic measurements are made at one or more locations on cellular ceramic body 12 at one or more temperatures T during the thermal processing temperature cycle T(t).

Figure 9:
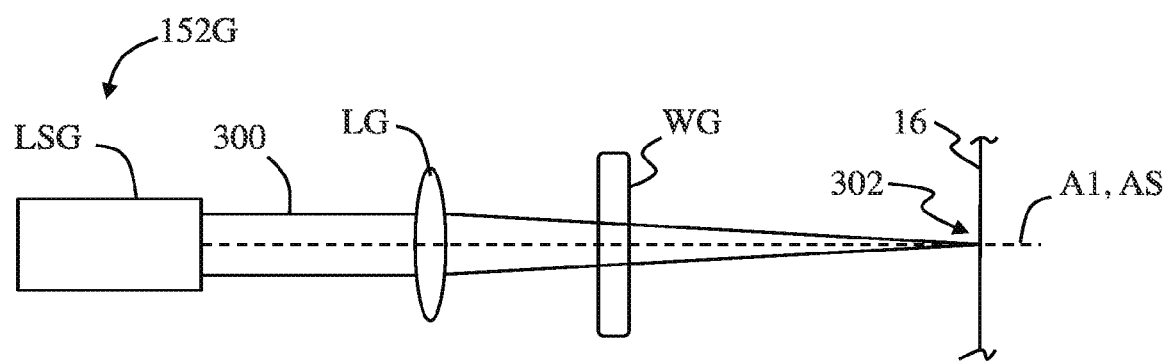
FIG. 9 is a close-up, schematic diagram of the generator side of the LBU measurement system end and the corresponding cellular ceramic body end.

For each temperature T at which an acoustic measurement of cellular ceramic body 12 is to be made, controller 160 generates a control signal SG and sends it to generator 152G, which in response thereto generates a modulated "generation" laser beam 300 that generates acoustic waves 320. FIG. 9 is a close-up, schematic diagram of the generator side of system 100, showing a generator laser LSG, focusing optical system LG, oven window WG and end 16 of cellular ceramic body 12. In response to control signal SG from controller 160, generator laser LSG creates generation laser beam 300, which is preferably modulated at frequency f of between about 1 kHz to about 5 MHz. Generation laser beam 300 is focused by focusing optical system LG and passes through oven window WG to form a focused spot 302 on the end 16 of cellular ceramic body 12 at wall intersection 14I. In an example embodiment, focusing optical system LG and laser LSG are adapted to perform scanning of generation laser beam 300, e.g., using scanning mirrors (not shown) so that modulated generation laser beam can be moved to different (e.g, adjacent) wall intersections 14I.

Figure 10:
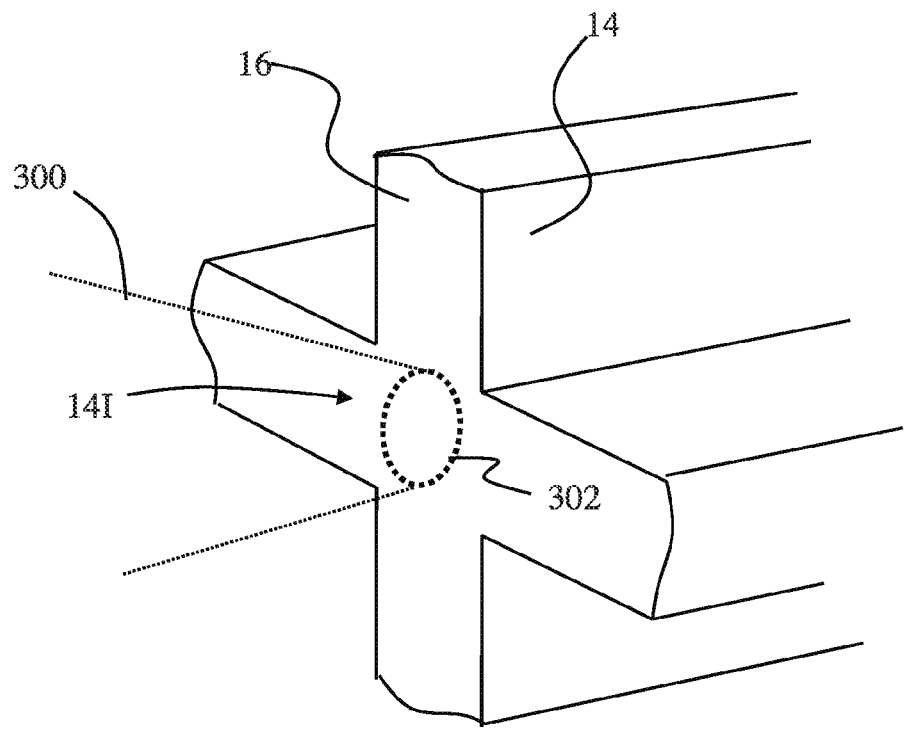
FIG. 10 is a close-up view of the generator end of the cellular ceramic body showing a generator focus spot on the wall intersection.

FIG. 10 is a close-up view of cellular ceramic body end 16 and wall intersection 14I showing focus spot 302 formed by focused laser beam 300. The rapid heating and cooling of the portion of wall intersection 14I caused by the modulation in generation laser beam 300 results in the generation of acoustic waves 320 having substantially the same modulation frequency f as laser beam 300. Acoustic waves 320 travel through a portion 12P of cellular ceramic body 12—namely, the portion of wall intersection 14I associated with focus spot 302—from one end 16 of cellular ceramic body to the opposite end 18 (see FIG. 5). Cellular ceramic body portion 12P is therefore also acoustic wave path of acoustic waves 120.

Figure 11:
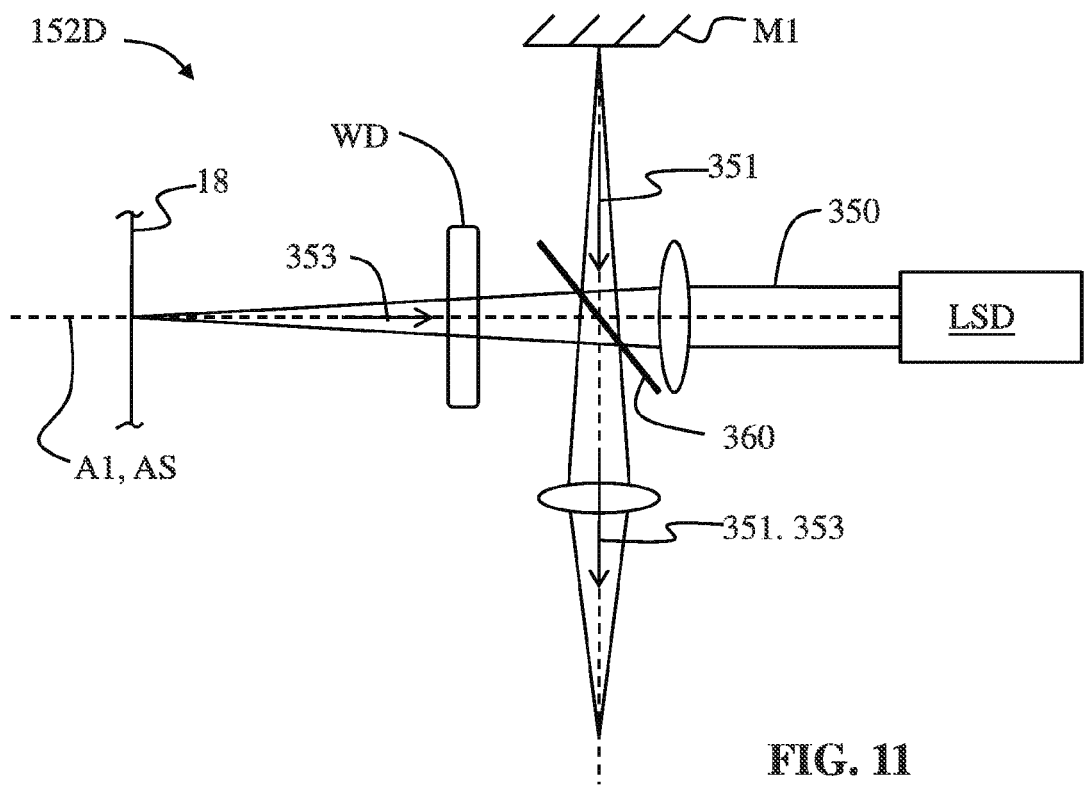
FIG. 11 is a close-up, schematic diagram of the detector side of the LBU measurement system and the corresponding cellular ceramic body end, and illustrates an example interferometric configuration for the detector.
Figure 12:
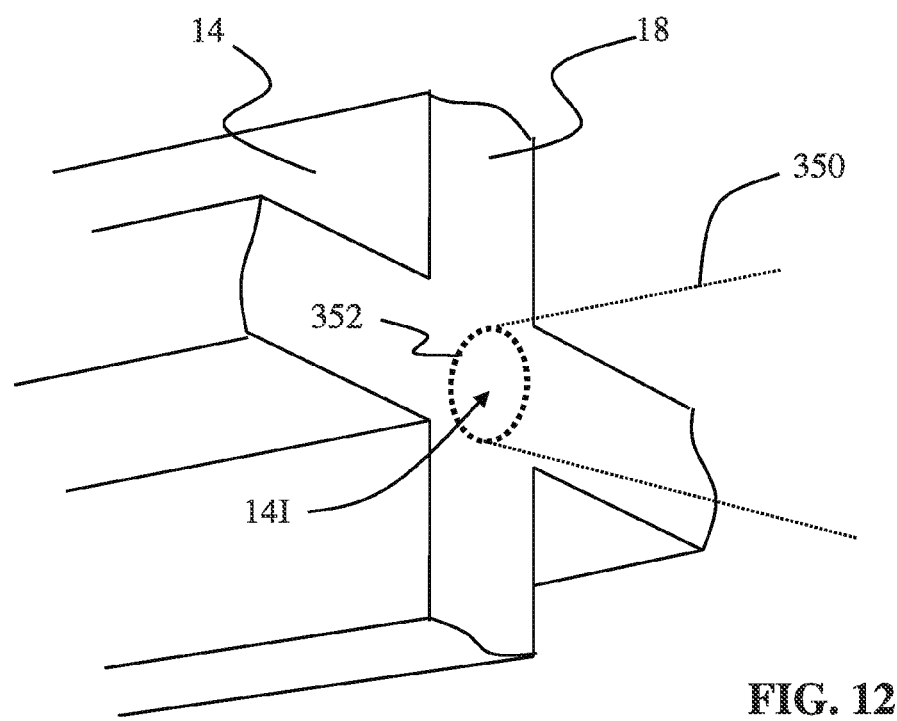
FIG. 12 is similar to FIG. 10 and shows the focus spot on the wall intersection formed by the focused detection laser beam at the detector end of the cellular ceramic body.

With reference also to FIG. 11, controller 160 sends a control signal SD to detector 152D, which causes the detector to generate a detection laser beam 350 via a laser LSD. Probe or "detection" laser beam 350 is focused by focusing optical system LD to form a focus spot 352 on the wall intersection 14I at cellular ceramic body end 18 that axially corresponds to the wall intersection 14I illuminated by focus spot 302 at end 16. A portion 351 of detection laser beam 350 is directed to a mirror M1 by a beamsplitter 360. Mirror M1 directs this laser beam portion 351 back through beamsplitter 360 where it is focused onto a photodetector 370 by a focusing optical system L1. Also, a portion 353 of detection laser beam 350 reflects from wall intersection 14I. This reflected laser beam portion travels out of oven interior 130 through oven window WD and is reflected toward photodetector 370 by beamsplitter 360 and is focused onto the photodetector by focusing optical system L1.

Detection beam portion 351 serves as a reference beam while detection beam portion 353 is imprinted with the acoustic wave information accumulated from propagating through cellular ceramic body 12 from opposite end 16 to end 18. Photodetector 370 generates electrical signal SD, which is representative of the interference of laser beams 351 and 353 and thus the measurement of the acoustic wave propagation through cellular ceramic body portion 12P. Electrical signal SD is sent to controller 160 for processing to extract time of flight information (i.e., speed of sound) and amplitude information, from which the elastic modulus E, the specific modulus E/$\rho$, and the attenuation can be calculated.

The time of flight (TOF) of ultrasonic waves 120 through honeycomb portion 12P is given by:

$$TOF = H/c_{mat},$$

where $c_{mat}$ is the "sonic velocity" in the cellular ceramic body.

The sonic velocity $c_{mat}$ for longitudinal portion 12P of cellular ceramic body 12 is thus calculated via the relationship:

$$c_{mat} = H/TOF$$

The specific modulus E/$\rho$ is proportional to the square of the sonic velocity, and is expressed in general form as:

$$E/\rho = k(\upsilon, d_{cell}, t_{wall}) \cdot c^2_{mat}$$

where k is a correction factor that includes Poisson's ratio $\upsilon$, which accounts for the cell cross-sectional geometry (circle, square, rectangle, hexagon, etc.), $d_{cell}$ is an average (ideal) diameter of the cells, and $t_{wall}$ is an average (ideal) wall thickness. Here, E is the Young's modulus of the structure and $\rho$ is its density.

The propagation of ultrasonic waves 120 through each longitudinal cellular ceramic body portion 12P is a relatively complex process. Dispersion, or the change in wave speeds at different frequencies, occurs as the initial ultrasonic pulse starts to propagate from cellular ceramic body end 16 to end 18. Also, the anisotropic material properties of walls 14 and their associated large porosity, including microcracking, also affect the mode of wave propagation and the sonic velocity.

The methods of the present disclosure use an ultrasonic frequency f in the range from approximately a 1 kHz to about 5 MHz. At these frequencies, the corresponding ultrasonic wavelength $\lambda$ (e.g., about 1 meter in air for 1 MHz) is much larger than the cell size (i.e., the cell width $W_C$) and the microstructural features (e.g., the pores and crystal domains) in walls 14.

Consequently, the underlying ceramic material appears substantially isotropic to ultrasonic waves 120. Further, the mode of ultrasonic wave propagation is also simplified so that it is non-dispersive at the test frequency f. Thus, the methods of the present disclosure set the correction factor k=1 as a reasonable simplification of otherwise complex ultrasonic wave propagation since the measurement technique seeks to obtain integrated (averaged) measurements of the elastic modulus E or specific modulus E/$\rho$.

Since k=1, the equation for the specific modulus becomes $$E/\rho = c^2_{mat},$$

so that the terms "specific modulus" and "square of the sonic velocity" become synonymous.

In an example embodiment, the attenuation or "integrated response" IR of ultrasonic waves 120 that propagate through longitudinal portions 12P is also measured. This attenuation can be expressed in decibels (dB) via the relationship:

$$IR(dB) = 10 \log(P).$$

where P is the measured ultrasonic power. Note that the measurement resolution for attenuation IR is essentially the same as that for the specific modulus E/$\rho = c^2_{mat}$.

In order to calculate the specific modulus E/$\rho$ for different locations on cellular ceramic body 12, generator 152G and detector 152D are periodically re-located (e.g., stepped) in on one or in two directions via translation stage signals SS from controller 160. In an example embodiment, generator 152G and detector 152D are stepped only along one axis (e.g., the X-axis) and measurements made at a number (e.g., 10 to 1000) of web intersections 14I along the given axis. In another example embodiment, generator 152G and detector 152D are stepped along two axes (e.g., the X and Y axes) and measurements made at a number (e.g., 10 to 1000) of web intersections 14I.

Each activation of generator 152G results in the generation of the aforementioned ultrasonic waves 120, which pass through the corresponding longitudinal portion 12P of substrate 12 and are subsequently detected by detector 152D. Upon detecting ultrasonic waves 120 at cellular ceramic body end 18, detector 152D generates electrical detector signal SD in response thereto. Detector signal SD is conducted to controller 160 and processor 164 therein as discussed above, or alternatively is provided to memory unit 166 where it is stored for later processing. The collection of electrical detector signals SD forms a raw data set $D_0$, which can be stored in memory unit 166 of controller 160 in a raw data set file. A number of such data sets ($D_{01}$, $D_{02}$, etc.) can be formed for different cellular ceramic bodies ("parts") 12 and stored for subsequent processing and analysis.

Acquiring a single detector signal SD at a given temperature T takes about a few seconds. Example cases of performing LBU measurements over a complete thermal processing cycle, i.e., from ambient to greater than about 1,000° C. and back to ambient, take about 20 hours. The response of the ceramic-forming material that makes up cellular ceramic body 12 may be dependent on the rate of heating and cooling in thermal cycle T(t). In an example embodiment, a 3° C./min heating rate is used, in combination with natural (i.e., unassisted) cooling. In an example embodiment, controlled forced cooling (e.g., via flowing nitrogen gas through oven interior 130) is used to reduce the measurement time and as a way of tailoring the temperature cycle T(t) to performing a thermal shock test.

In an example embodiment, processor 164 is configured (e.g., via instructions in memory unit 166) to determine (i.e., calculate) at least one of a number of material parameters associated with the raw waveform of the acoustic response as embodied in acoustic waves 120 and detector signal SD. These material parameters include the time of flight TOF, the speed of sound in the material $c_{mat}$ (via time of flight measurement, as discussed above), the peak frequency and bandwidth (through a fast-Fourier transform (FFT) frequency response), acoustic wave amplitude versus time, the elastic modulus E, the specific modulus $E/\rho=c^2_{mat}$, and the attenuation as measured by the peak amplitude change from input end 16 to output end 18. In an example embodiment, processor 164 processes detector signals SD stored in raw data set $D_0$ and calculates the at least one material parameter for select spatial positions on cellular ceramic body 12 and for select temperatures T in the temperature cycle T(t).

In an example embodiment, the temperature dependence of one or more of the extracted material parameters reveals itself in the form of a hysteresis curve. An evaluation of one or more hysteresis curves at multiple cellular ceramic body locations (i.e., for multiple cellular ceramic body portions 12P) is used to determine the quality of cellular ceramic body 12, e.g., by comparing measured material parameter values to threshold values based on one or more product specifications. For example, the elastic modulus E is one of the microstructural material properties that has been found useful in predicting the thermal regeneration performance of DPFs formed from fired cellular ceramic bodies 12.

In an example embodiment, the hysteresis of the elastic modulus E is used to determine an amount of thermal-mechanical stress that a cellular ceramic body 12 might experience in operation. In an example embodiment, this determination is aided by the use of numerical simulations to arrive at a quantitative stress threshold value. This stress threshold value is used to predict whether a particular cellular ceramic body 12 will survive under its anticipated operating conditions based on its inherent properties, as opposed to properties it obtains through post-processing (e.g., by coatings used to form a DPF).

In an example embodiment, multiple hysteresis curves for different cellular ceramic body portions 12P are used to assess material homogeneity of cellular ceramic body 12, and can be used in stress calculations to predict survivability based on one or more threshold stress specifications.

Figure 13:
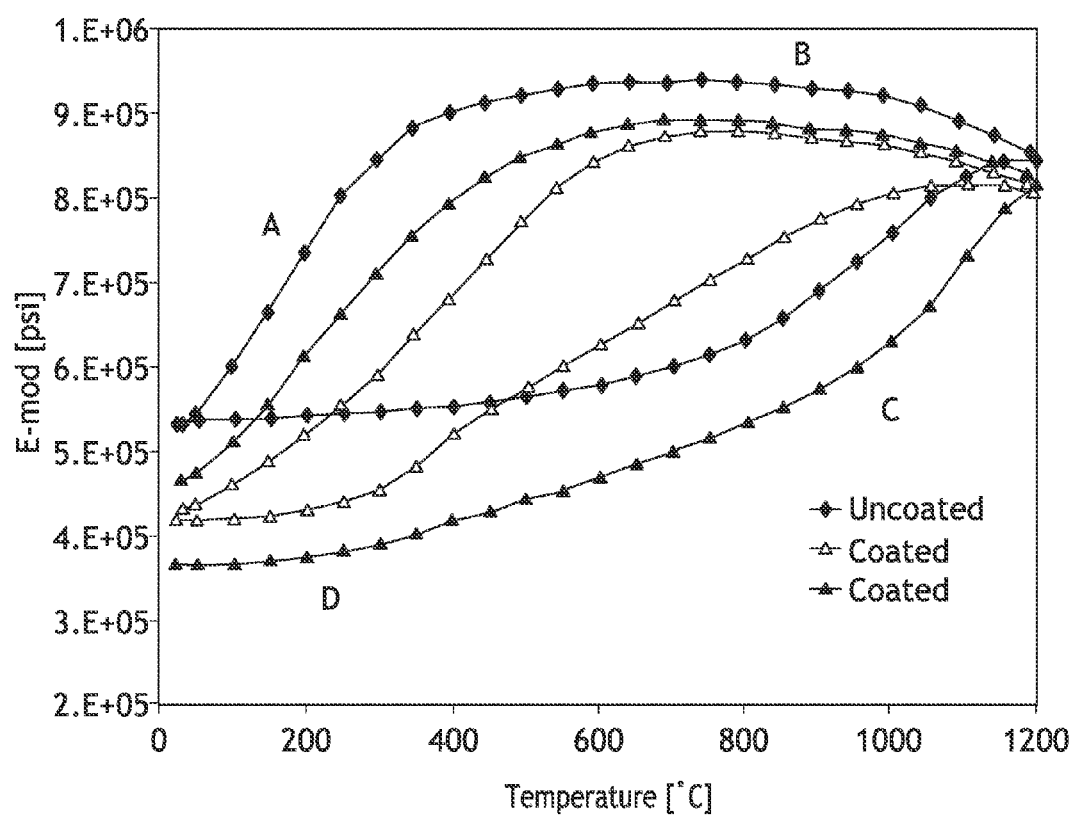
FIG. 13 is an example plot elastic modulus E (psi) vs. temperature T (° C.) that illustrates the hysteresis commonly observed over a temperature cycle when measuring the elastic modulus of cellular ceramic bodies used to form diesel particulate filters.

FIG. 13 is an example plot elastic modulus E (psi) vs. temperature T (° C.) that illustrates the hysteresis commonly observed over a temperature cycle when measuring the elastic modulus of cellular ceramic bodies 12 used to form DPFs. The different curves correspond to an uncoated cellular ceramic body 12, as well as to coated cellular ceramic bodies. Cellular ceramic bodies 12 are typically coated when used as DPFs, and measurement of coated and uncoated cellular ceramic bodies is one way of determining whether filter coatings have been applied properly.

The hysteresis plot of FIG. 13 has four regions, identified as A through D. Region A corresponds to the initial temperature increase and indicates an increasing number of microcracks as evidences by the increase in the elastic modulus E. Region B corresponds to a region of continuing temperature increase and the relatively flat slope indicates that the number of microcracks is roughly constant or even slightly decreasing. Region C corresponds to a region of initial temperature decrease and indicates a decrease in microcracks. Region D corresponds to a region of continuing temperature decrease down to ambient temperature and indicates a relatively constant number of microcracks.

Figure 14:
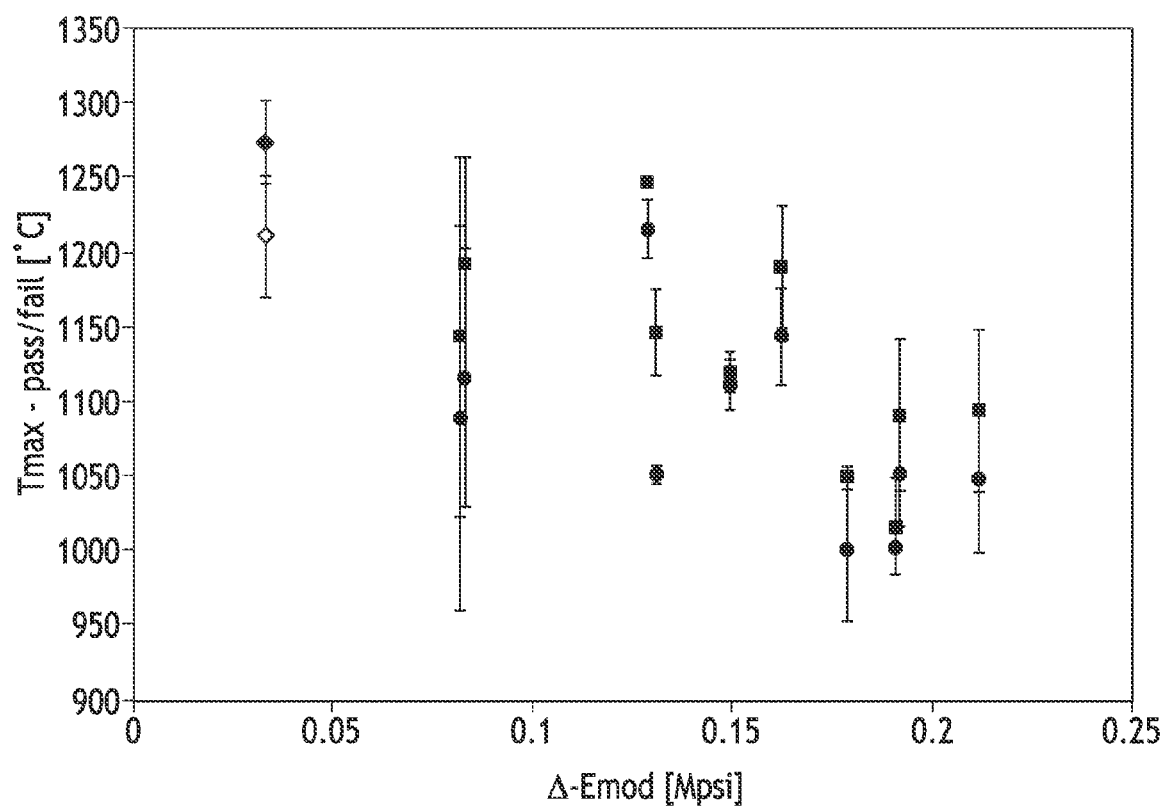
FIG. 14 plots the maximum pass/fail temperature $T_{MAX}$ (° C.) versus the change in elastic modulus $\Delta E$ (Mpsi) and illustrates the correlation between the thermal survivability temperature during DPF regeneration and the measured elastic modulus values using the methods of the present disclosure.

FIG. 14 plots the maximum pass/fail temperature $T_{MAX}$ (° C.) versus the change in elastic modulus $\Delta E$ (Mpsi), and illustrates the correlation between a thermal survivability temperature during DPF regeneration and the measured elastic modulus values using the methods of the present disclosure. In the plot, the solid circles indicate a coated DPF that passed and the solid squares indicated a coated DPF that failed. Also, the open diamonds indicate an uncoated DPF that passed and the solid diamonds indicate an uncoated DPF that failed.

Figure 15:
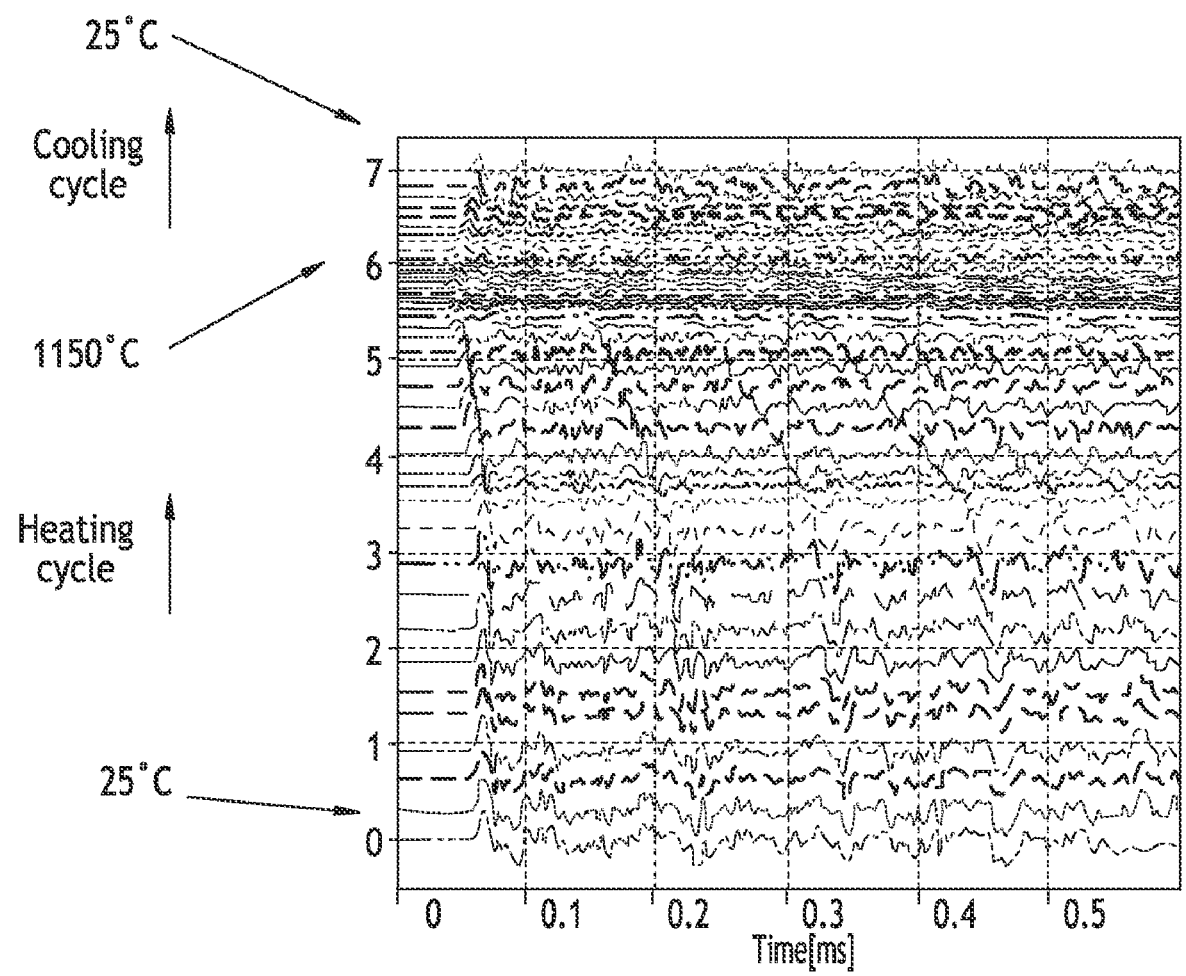
FIG. 15 is a "waterfall" plot of the ultrasonic response (amplitude) versus time (s) taken at a select location at various temperatures during the thermal cycle, which starts at 25° C., ramps up to 1150° C. and then returns to 25° C.

FIG. 15 is a "waterfall" plot of the ultrasonic response (amplitude) versus time (s) taken at a select location at various temperatures during the thermal cycle, which starts at 25° C., ramps up to 1150° C. and then returns to 25° C. Note the change in the acoustic waveform as a function of temperature.

The data for specific modulus $E/\rho$ collected using the present disclosure shows substantial detail about the variations in specific modulus as a function of position and temperature. This, in turn, provides much more information about the variations in the structure and material properties of cellular ceramic body 12, and in particular about the frequency of the material variations therein. Having a greater resolution for measurements of specific modulus $E/\rho$ allows easier discernment of the nature of the material variations, which therefore allows production problems to be more readily diagnosed and fixed.

Figure 16:
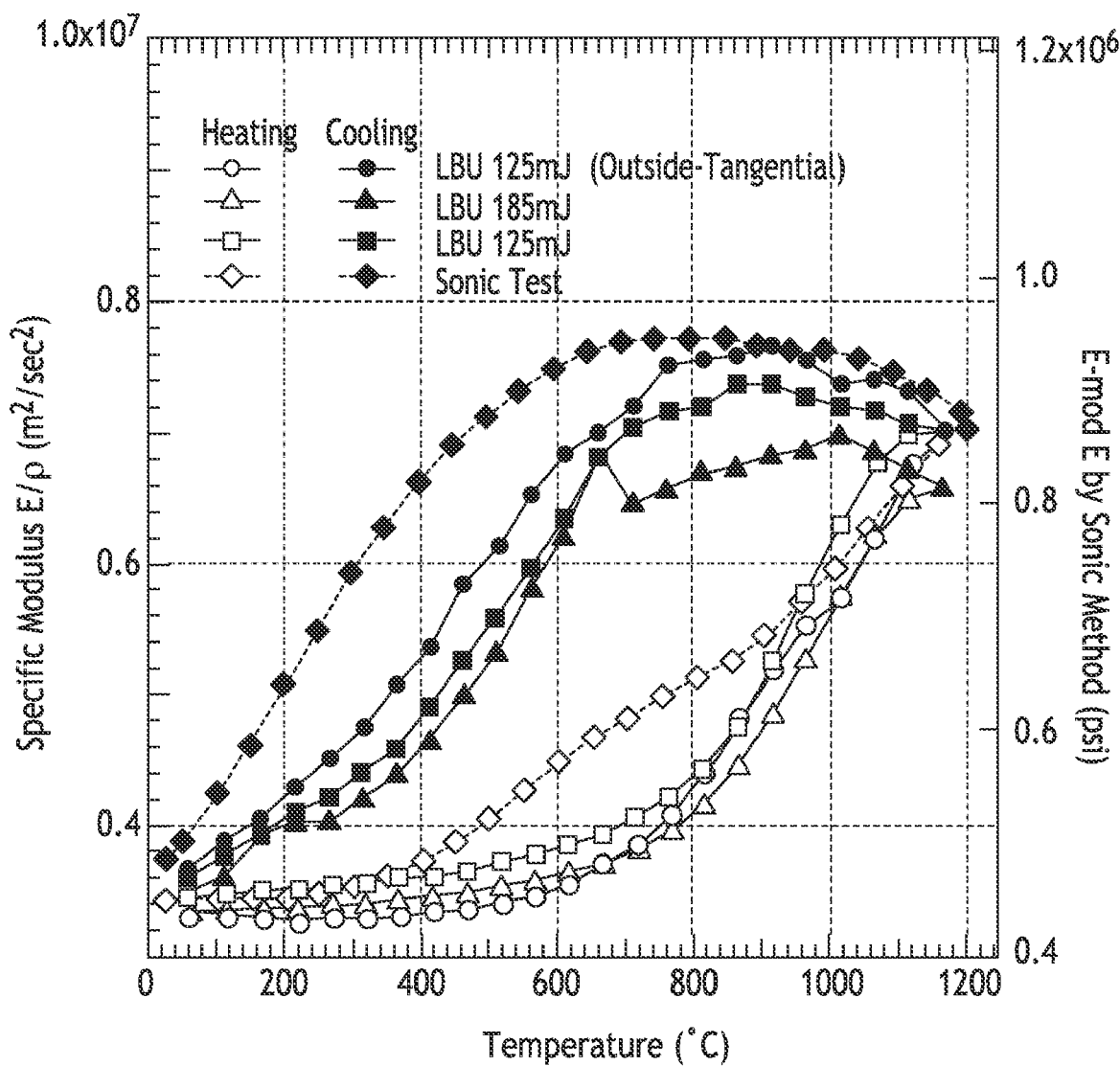
FIG. 16 is a plot of the specific modulus $E/\rho$ ($m^2/s^2$) (left-hand axis) versus temperature T (° C.) for measurements taken using the LBU-based methods of the present disclosure, as compared to the prior art ultrasonic "sonic" measurements of elastic modulus E (right-hand axis)

FIG. 16 is a plot of the specific modulus E/ρ (m²/s²) (left-hand axis) versus temperature T (° C.) for measurements taken using the LBU-based methods of the present disclosure as compared to the prior art ultrasonic ("sonic") test that measures the elastic modulus E (psi) (right-hand axis). The energies of the three LBU-based measurements are represented in milliJoules (mJ).

Figure 17:
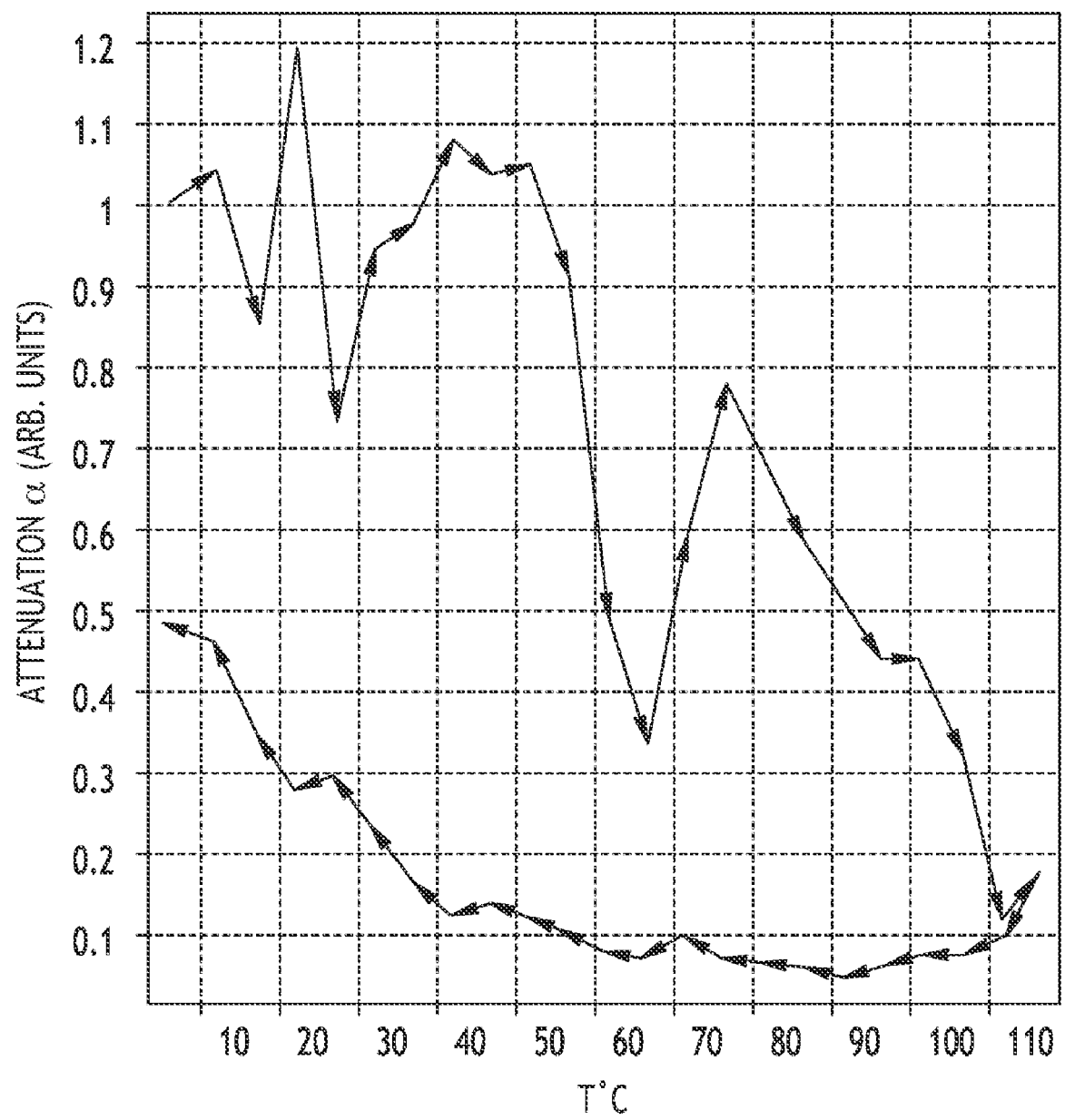
FIG. 17 plots the ultrasonic attenuation a (arbitrary units) as a function of temperature T (° C.) for an example cellular ceramic body, with the arrows indicating the time evolution of the hysteresis.

FIG. 17 plots the ultrasonic attenuation a (arbitrary units) as a function of temperature T (° C.) for an example cellular ceramic body 12, with the arrows indicating the time evolution of the hysteresis.

Figure 18:
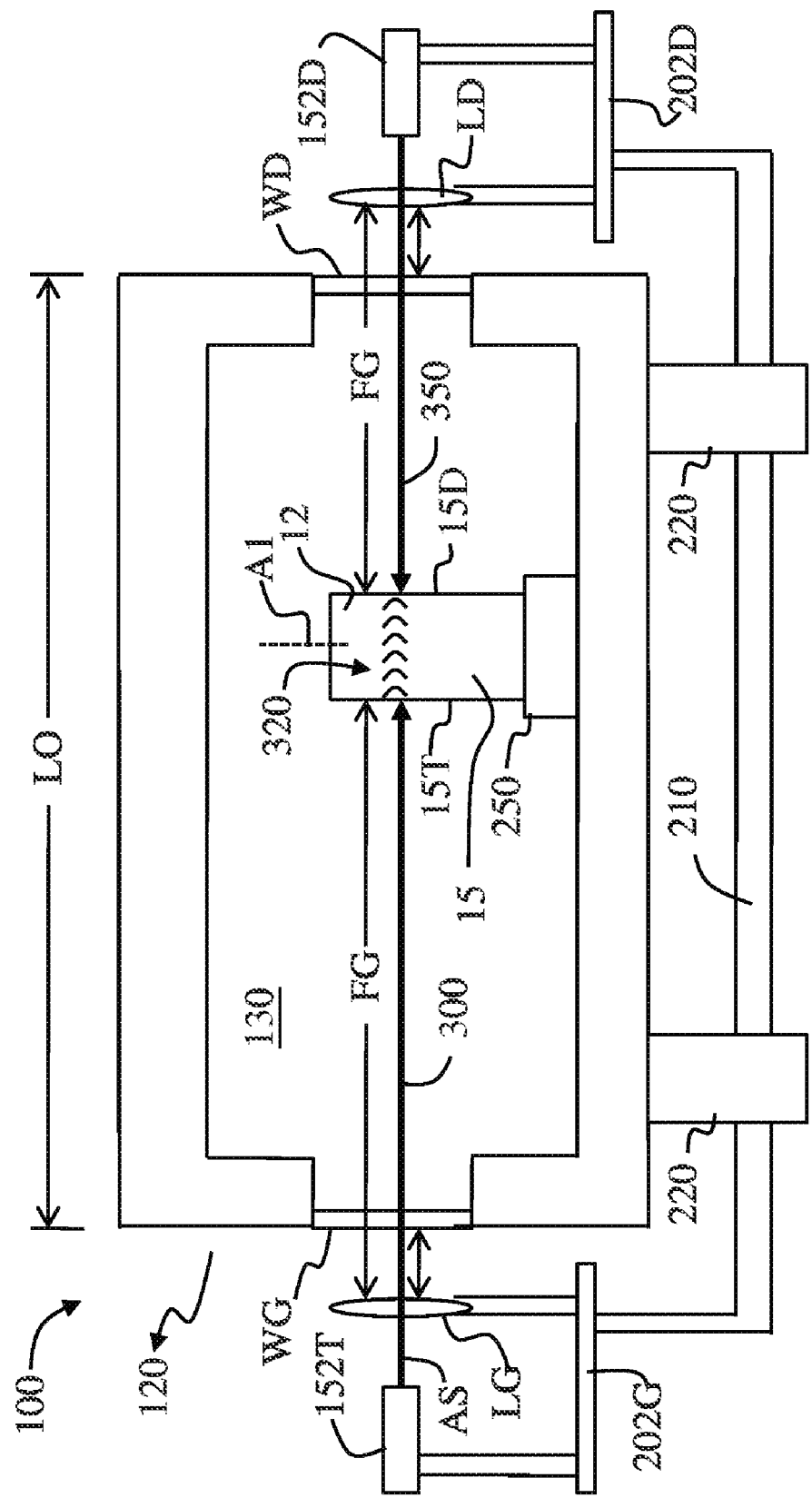
FIG. 18 is similar to FIG. 5, but shows the cellular ceramic body arranged vertically, i.e., with its central axis along in the Z-direction and perpendicular to the system axis.
Figure 19:
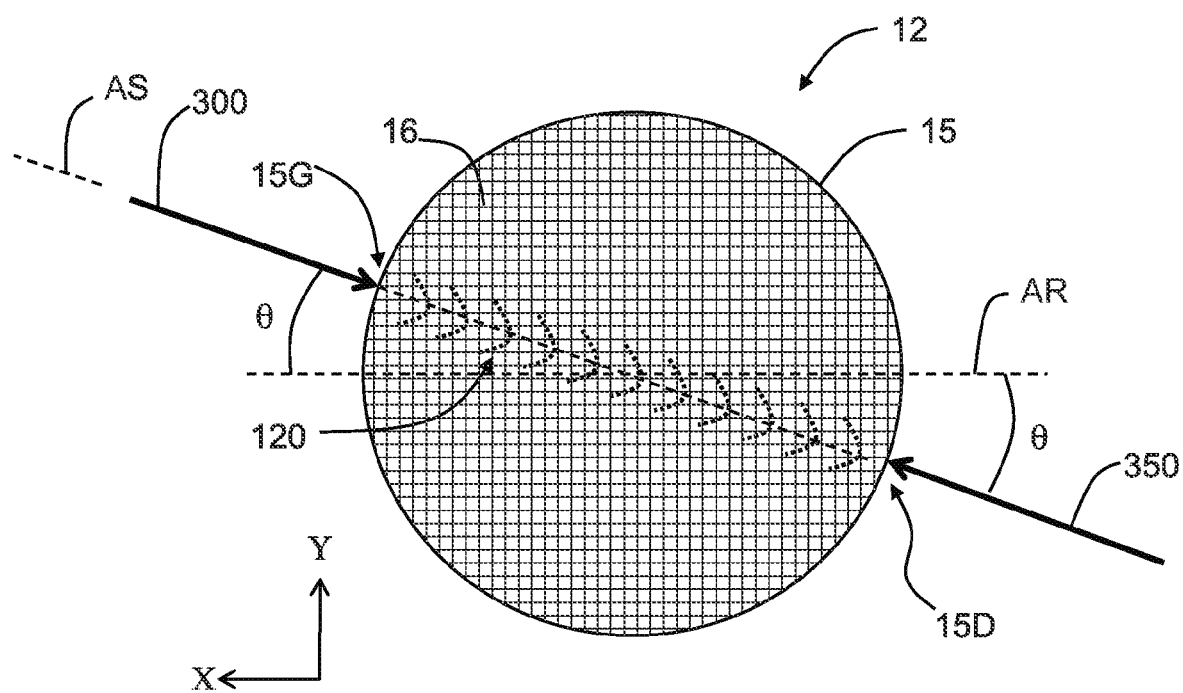
FIG. 19 is an end-on view of the cellular ceramic body showing the generator and detection laser beams incident on respective generation and detection locations on the structure's outer wall.

FIG. 18 is similar to FIG. 5, but shows cellular ceramic body 12 arranged vertically, i.e., with its central axis A1 in the Z-direction. Modulated laser beam 300 is incident upon outer wall 15 at a generation location 15G, and generates acoustic waves 120 that travel substantially radially through cellular ceramic body portion 12P to the opposite side of the outer wall at a detection location 15D. Detection laser beam 350 is directed to be substantially incident upon outer wall location 15D to detect the propagated acoustic waves 120. With reference to FIG. 19, generation location 15G and detector location 15D need not be exactly 180° from one another, as the propagation through the network of walls 14 is relatively complex. The generation/detection angle θ of system axis AS is measured relative to a reference axis AR.

Figure 20:
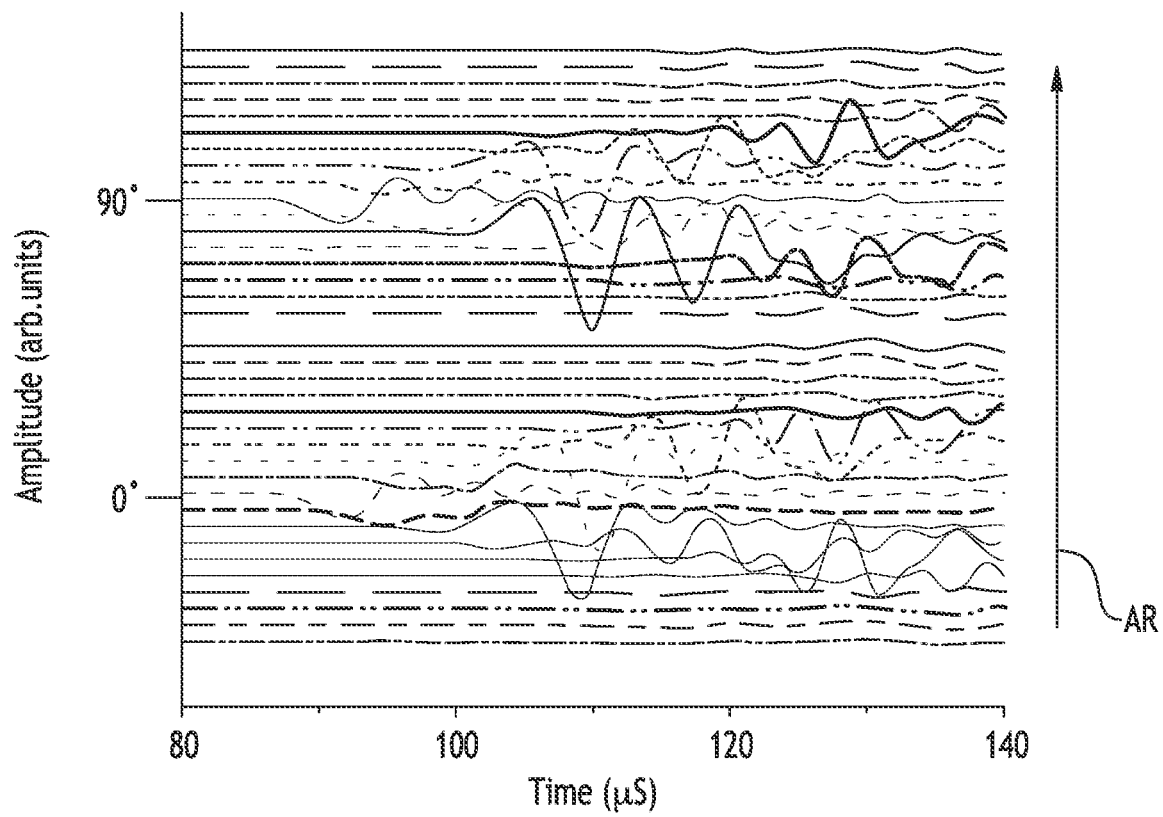
FIG. 20 is a plot of the acoustic wave amplitude (arbitrary units) versus time (s) for a range of generation/detection angles θ (degrees)

FIG. 20 is a plot of the acoustic wave amplitude (arbitrary units) versus time (s) for a range of generation/detection angles θ (degrees) (see FIG. 19), where the angular increment Δθ=5° in the direction indicated by arrow AR. In an example embodiment, the change in angle θ is accomplished by an automated rotation of support member 250, while in another example embodiment, it is accomplished by changing the angles of modulated laser beam 300 and detection laser beam 350. It can be seen from the plot of FIG. 20 that there is a "dead zone" over an angular range of about 45°, which indicates the presence of a crack in cellular ceramic body 12.

Figure 21:
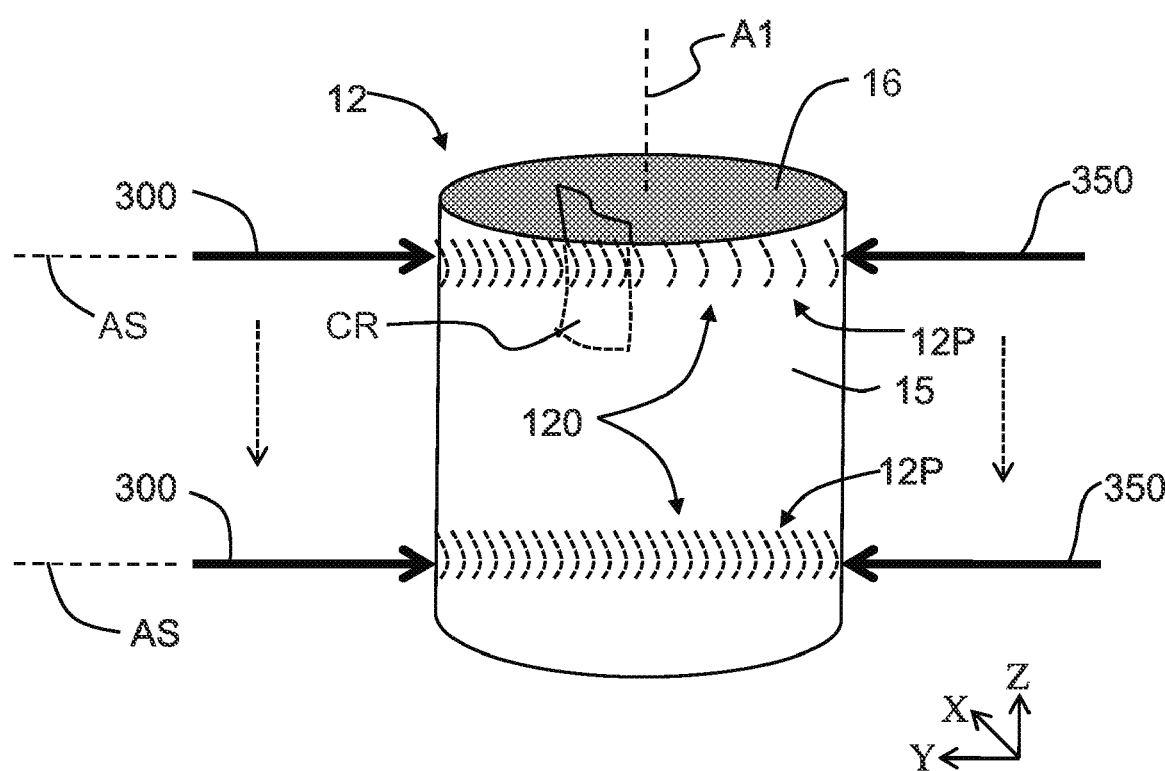
FIG. 21 is a close-up side view of the cellular ceramic body showing the generator and detection laser beams varying in height along the Z-direction when measuring a vertically oriented cellular ceramic body.

FIG. 21 is a close-up side view of cellular ceramic body 12 showing generation and detection laser beams 300 and 350 varying in height along the Z-direction. Cellular ceramic body 12 is shown as having an internal crack CR near end 16. Generation and detection laser beams 300 and 350 are varied in height (Z) relative to cellular ceramic body 12 by adjusting translation stages 202T and 202D, for example, or by scanning the generation and detection laser beams using the corresponding focusing optical systems LG and LD. The resultant measurements provide information along substantially radial lines of cellular ceramic body 12. FIG. 21 schematically illustrates how crack CR changes acoustic waves 120 when the acoustic waves and the crack are both within cellular ceramic body portion 12P.

Figure 22:
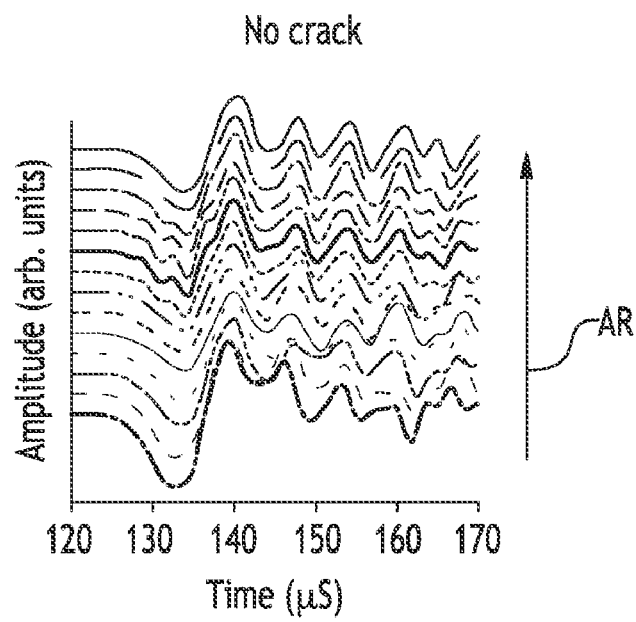
FIG. 22 plots the acoustic wave amplitude (arbitrary units) vs. time (s) for different generator and detector positions, in increments of 1 cm in the Z-direction, for a cellular ceramic body having no internal cracks.

FIG. 22 plots the acoustic wave amplitude (arbitrary units) vs. time (s) for different transmission and detection positions 15G and 15D in increments of 1 cm (i.e., 1 cm per line, as measured from a "good surface") in the Z-direction (arrow AR) for a cellular ceramic body 12 having no internal cracks. As seen in the plot, each of the acoustic wave amplitude traces shows significant variations in amplitude as a function of time.

Figure 23:
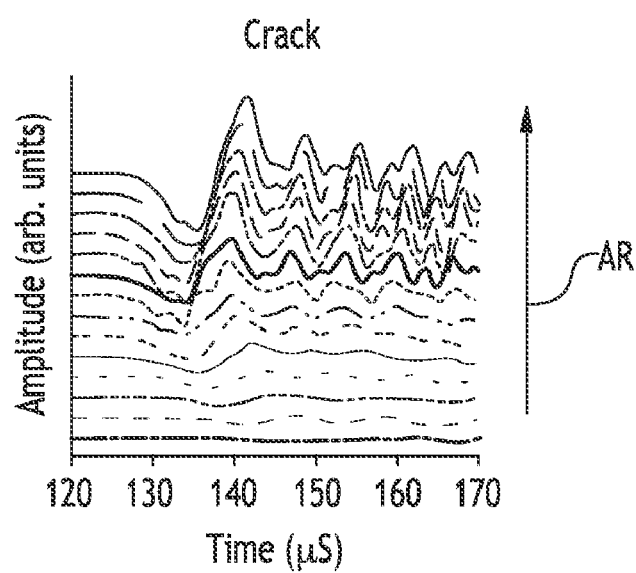
FIG. 23 is the same plot as FIG. 22, but for a cellular ceramic body having internal cracks, and illustrating how the acoustic wave traces are used to estimate the size of the internal crack.

FIG. 23 is the same plot as FIG. 22 except it is for a cellular ceramic body having an internal crack. A number of the acoustic wave amplitude traces—about seven of them—show a greatly diminished amplitude relative to the others, which is indicative of an internal crack having a size of about 7 cm in length. Thus, in an example embodiment, one of the measured material properties of cellular ceramic body 12 includes "cracking."

As with LBU measurements performed on cellular ceramic body 12 oriented in the horizontal direction, LBU measurements are performed on the cellular ceramic body oriented in the vertical direction as a function of temperature during thermal processing.

In testing cellular ceramic bodies 12, it is not always easy to align transmission and detection laser beams 300 and 350 to focus on web intersections 14I. Displacement of a cellular ceramic body 12 can occur at high temperatures so that good alignment at ambient temperature can be lost. This causes either reduced signal amplitude or a complete loss of signal.

Figure 24:
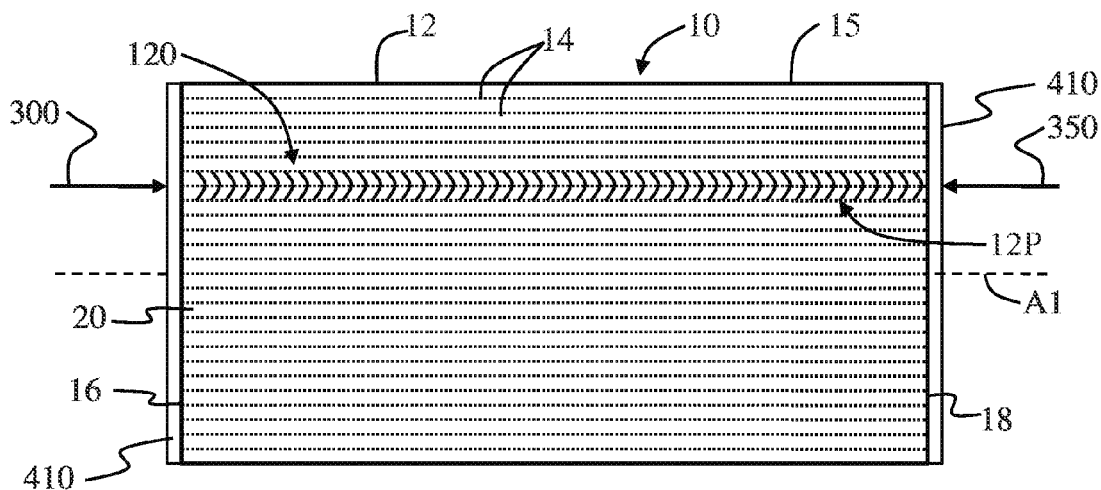
FIG. 24 and FIG. 25 are similar to FIG. 2 and illustrate an example embodiments where a coupling layer is applied to the respective ends of a ceramic cellular body to ensure the transmission and detection laser beams are coupled to and generate acoustic waves in the ceramic cellular body rather than passing through one or more of the cells.

To overcome this problem, with reference to FIG. 24 in an example embodiment, a thin coupling layer 410 of inorganic material is applied to ceramic body ends 16 and 18. After coupling layers 410 are applied, they are dried before an LBU measurement is made. In an example embodiment, coupling layers 410 are about 1 mm thick. Coupling layers 410 help laser beams 300 and 350 maintain a more consistent contact with cellular ceramic body 12 throughout the temperature cycle.

In an example embodiment, coupling layers 410 comprise the type of ceramic paste normally used for plugging DPFs, and can be used on sonic bar type, flow-through type, or DPF types of cellular ceramic bodies 12. Coupling layers 410 facilitate proper coupling of laser beams 300 and 350 to cellular ceramic body 12 by ensuring that the laser beams always impinge on a solid material at respective ends 16 and 18. This results in the generation of acoustic waves 120 along the solid web of walls 14 rather than having the laser beams travel mostly or entirely through one or more cells 20.

Figure 25:
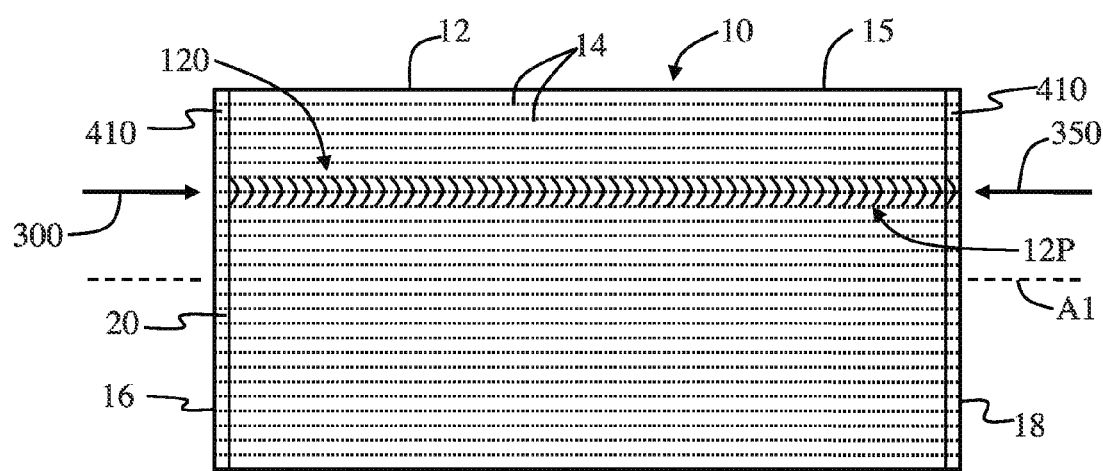

An example ceramic paste used for coupling layers 410 is prepared via the procedures for regular plugging purposes. For example, 50% coarse cordierite and 50% fine cordierite, both crumbled and granularized or powderized from sintered cordierite product, are mixed with added Methocel, Ludox and water to make a paste. Such a paste has a close match to the material properties of the underlying cellular ceramic body 12. The past is applied, smeared and flattened onto the two ceramic body ends 16 and 18 so that each end surface is covered. With reference to FIG. 25, coupling layers 410 may be applied in a manner that plugs cells 20. Coupling layers 410 are then dried, e.g., at 50° C. for one to two hours. After drying, coupling layers 410 are polished to make the exposed surface thereof smooth and flat. Cellular ceramic body 12 is then ready for LBU measurement using the methods described above.

It will be apparent to those skilled in the art that various modifications to the example embodiments of the disclosure as described herein can be made without departing from the spirit or scope of the disclosure as defined in the appended claims. Thus, it is intended that the present disclosure covers the modifications and variations of this disclosure provided they come within the scope of the appended claims and the equivalents thereto.

What is claimed is:

1. A method of measuring at least one material property of a ceramic cellular ceramic body during thermal processing, comprising:
   a) subjecting the ceramic cellular ceramic body to a temperature cycle within an interior of an oven having first and second windows;
   b) sequentially irradiating with a first laser beam from a first laser the cellular ceramic body through the first window at one or more first locations to generate acoustic waves in the cellular ceramic body;
   c) sequentially irradiating with a second laser beam from a second laser the cellular ceramic body through the second window at one or more second locations that correspond to the one or more first locations to detect the acoustic waves in the cellular ceramic body; and d) calculating from the detected acoustic waves the at least one material property.

2. The method of claim 1, further comprising:
forming from the detected acoustic waves corresponding one or more electrical detector signals; and
calculating the at least one material property from the one or more electrical detector signals.

3. The method of claim 1, wherein the cellular ceramic body includes a central axis, the first and second laser beams are aligned along a system axis, and further including:
supporting the cellular ceramic body using a support fixture so that the central axis is either substantially aligned with or is substantially perpendicular to the system axis.

4. The method of claim 1, wherein the at least one material property is selected from the group of material properties comprising: time of flight (TOF), speed of sound $c_{mat}$, peak frequency and bandwidth, acoustic wave amplitude versus time, elastic modulus E, cracking, and specific modulus $E/\rho=c^2_{mat}$, where $\rho$ is a material density, and attenuation.

5. The method of claim 1, further comprising modulating the first laser beam at a frequency between 1 kHz and 5 MHz.

6. The method of claim 1, wherein the cellular ceramic body comprises a cylinder and has associated therewith an axial direction and a radial direction, further comprising:
sending the acoustic waves through the cellular ceramic body in either substantially the axial direction or in substantially the radial direction.

7. The method of claim 1, wherein the cellular ceramic body includes a plurality of walls that define a plurality of cells and wall intersections, and further comprising sequentially focusing the first laser beam onto different wall intersections.

8. The method of claim 1, further comprising repeating acts b) through d) for a plurality of temperatures in the temperature cycle and calculating the at least one material property as a function of temperature.

9. The method of claim 1, further comprising providing first and second coupling layers at respective first and second ends of the cellular ceramic body so that the first and second laser beams are respectively incident thereon.

10. The method of claim 8, further comprising measuring a hysteresis of at least one material property as a function of temperature.

11. The method of claim 9, wherein the first and second coupling layers are made of a ceramic-based material.

12. The method of claim 11, wherein the cellular ceramic body includes a plurality of cells that are open at the first and second ends, and including providing the first and second coupling layers as plugs in the open cells at the first and second open ends.

13. A method of measuring at least one material property of a ceramic cellular ceramic body during thermal processing, comprising:

a) arranging ceramic cellular ceramic body in an oven having an adjustable temperature and first and second windows;

b) adjusting the oven temperature, and for each of a plurality of oven temperatures:
sequentially irradiating the cellular ceramic body at a plurality of first locations with a modulated laser beam from a first laser, with the modulated laser beam passing through a first window to generate acoustic waves over a plurality of acoustic paths within the ceramic cellular body;

c) sequentially irradiating the cellular ceramic body at a plurality of second locations that correspond to the plurality of the first locations through the second window using a detection laser beam from a second laser to detect the acoustic waves for the plurality of acoustic paths and forming a corresponding plurality of electrical detector signals representative of the detected acoustic waves; and d) calculating from the plurality of electrical detector signals the at least one material property as a function of location and temperature.

14. The method of claim 13, wherein the at least one material property is selected from the group of material properties comprising: time of flight (TOF), speed of sound $c_{mat}$, peak frequency and bandwidth, acoustic wave amplitude versus time, elastic modulus E, specific modulus $E/\rho=c^2_{mat}$ where $\rho$ is a material density, and attenuation.

15. The method of claim 13, wherein the cellular ceramic body comprises a cylinder and has associated therewith an axial direction and a radial direction, further comprising:
sending the acoustic waves through the cellular ceramic body in either substantially the axial direction or in substantially the radial direction.

16. The method of claim 13, wherein the cellular ceramic body includes a plurality of walls define a plurality cells and a plurality of wall intersections, and further comprising focusing the modulated laser beam onto a wall intersection.

17. The method of claim 13, further comprising providing first and second coupling layers at respective first and second ends of the cellular ceramic body so that the modulated and detection laser beams are respectively incident thereon.

18. The method of claim 13, further comprising measuring a hysteresis of at least one material property as a function of temperature.

19. The method of claim 17, wherein the first and second coupling layers are made of a ceramic-based material.

20. The method of claim 17, wherein the cellular ceramic body includes a plurality of cells that are open at the first and second ends, and including providing the first and second coupling layers as plugs in the open cells at the first and second open ends.

* * * * *